United States Patent [19]

Gradeff et al.

[11] Patent Number: 4,663,439

[45] Date of Patent: * May 5, 1987

[54] PROCESS FOR THE PREPARATION OF CERIC ALKOXIDES

[75] Inventors: Peter S. Gradeff, Pottersville; Fred G. Schreiber, Highland Park, both of N.J.

[73] Assignee: Rhone-Poulenc, Inc., New Brunswick, N.J.

[*] Notice: The portion of the term of this patent subsequent to Dec. 18, 2001 has been disclaimed.

[21] Appl. No.: 674,640

[22] Filed: Nov. 26, 1984

[51] Int. Cl.$^4$ .............................................. C07F 5/00
[52] U.S. Cl. ...................................................... 534/15
[58] Field of Search ........................................ 534/15

[56] References Cited

U.S. PATENT DOCUMENTS

| | | | |
|---|---|---|---|
| 3,479,381 | 11/1969 | Mitchell | 534/15 |
| 3,631,081 | 12/1971 | Huggins et al. | 534/15 |
| 3,757,412 | 9/1973 | Mazdiyasni et al. | 534/15 |
| 4,489,000 | 12/1984 | Gradeff et al. | 260/429.2 |
| 4,492,655 | 1/1985 | Gradeff et al. | 534/15 |
| 4,507,245 | 3/1985 | Ozaki et al. | 534/15 |

Primary Examiner—Edward A. Miller

[57] ABSTRACT

A process is provided for preparing ceric alkoxides, which comprises reacting ceric ammonium nitrate complexed with and in solution in ethylene or propylene glycol ether or tetrahydrofuran with an anhydrous alkali metal alkoxide at a temperature within the range from about −30° C. to about 200° C., preferably from 0° to about 150° C., until ceric alkoxide and the nitrate salt of the base are formed; the nitrate formed during the reaction is insoluble in the glycol ether and tetrahydrofuran and can be separated from the reaction mixture, and the cerium alkoxide when soluble in the glycol ether or tetrahydrofuran can be isolated from the solution pure, or as the complex with the alcohol or with the solvent, or in some cases the alkoxide can be used without separation from the reaction mixture in the presence of the nitrate.

10 Claims, No Drawings

PROCESS FOR THE PREPARATION OF CERIC ALKOXIDES

Polyvalent metal alkoxides are an important class of versatile organometallic compounds that have many industrial uses. In some instances their uses parallel the metal carboxylates and other organometallic compounds, but they have advantages over such compounds because of their catalytic properties, ease of hydrolysis, solubility in organic solvents, and volatility. They have been used as paint additives, water repellents, adhesion promoters, mordants, sizing agents in enamel compositions, catalysts and also very importantly as intermediates in synthesis of other organic compounds.

There are four general preparative methods for metal alkoxides, all under anhydrous conditions, as follows:

A. By reaction of the corresponding alcohol and metal, such as the alkali metals, alkaline earth metals, and aluminum, with the assistance of an alkaline or acidic catalyst.

B. By reaction of the corresponding alcohol with the oxides and hydroxides of the metal, for instance NaOH or $Na_2O$, $V_2O_5$ and $MoO_3.2H_2O$.

C. By reaction of the corresponding alcohol and metal halide in the presence of an anhydrous base. A typical example is the preparation of $Th(OR)_4$ or $Zr(OR)_4$:

$$ThCl_4 + 4ROH + 4NaOR \rightarrow Th(OR)_4 + 4NaCl$$

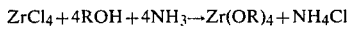

$$ZrCl_4 + 4ROH + 4NH_3 \rightarrow Zr(OR)_4 + NH_4Cl$$

The reaction can be used for preparing alkoxides of titanium, hafnium, germanium, niobium, tantalum, aluminum and tin.

D. By transetherification of the metal alkoxides of lower alcohols, such as the methoxides, ethoxides or isopropoxides, with a higher alcohol.

Method A is exemplified for a number of yttrium, lanthanum and other lanthanide alkoxides by L. Brown and K. Mazdiyasni in *Inorganic Chemistry*, (1970) 2783. The reaction, previously thought to be useful only for the alkali metals, magnesium and aluminum, was extended by them to the synthesis of yttrium and all of the lanthanide isopropoxides. For the lower lanthanides, such as lanthanum, cerium, praesodymium and neodymium, a mixture of $HgCl_2$ and $Hg(C_2H_3O_2)_2$ or $HgI_2$ is used as a catalyst, to increase both the rate of reaction and percent yield. Generally, 5 g of metal turnings is reacted with about 300 ml of isopropyl alcohol at reflux temperature for about 24 hours and in the presence of a small amount of Hg salt catalyst. The yields are said to be 75% or better.

Most of the other examples in the literature of the preparation of alkoxides of lanthanides refer to the use of the corresponding metal halides. In some cases, a complex $LaCl_3.3ROH$ is preferred to the $LaCl_3$ (Misra et al, *Austr J Chem* 21 797 (1978) and Mehrotra and Batwara, *Inorganic Chem* 9 2505 (1970)).

An interesting variation of Method D is mentioned by Tripathi, Batwara, and Mehrotra *J. C. S. A.* 1967 991. Lower ytterbium alkoxides (such as the methoxide and ethoxide) were synthesized from ytterbium isopropoxide, by transetherification with methanol or ethanol. Owing to their sparing solubility, these alcohols were removed by precipitation as the reaction proceeded, driving the transetherification to completion.

In general, Methods A, B and C are only suited for preparation of the lower alkoxides, such as the methoxides, ethoxides and isopropoxides, since the reactivity of higher alcohols diminishes with increase in their molecular weights. The higher alkoxides are better prepared by Method D, which is a two-step process.

The only published method for preparing ceric alkoxides applied Method C to ceric chloride, Bradley et al, *J. C. S.* 1956 2260–64. Since cerium tetrachloride is unstable, the dipyridinium cerium hexachloride complex was Bradley et al's choice as starting material.

Cerium dioxide was first converted to ceric ammonium sulphate. Pure ceric hydroxide was precipitated from an aqueous solution of ceric ammonium sulfate and washed thoroughly. The freshly-prepared ceric hydroxide, suspended in absolute alcohol, was treated with anhydrous hydrogen chloride and then pyridine was added, which formed the insoluble dipyridinium cerium hexachloride complex $(Py)_2CeCl_6$. The complex was filtered, dried, and used for preparing the methoxide, ethoxide and isopropoxide directly, while the propyl, butyl, secondary butyl, neopentyl and n-pentyl alkoxides were made by alcohol interchange, i.e., transetherification, from the isopropoxide. The methoxide and ethoxide were also made by exchange from the isopropoxide.

In accordance with the invention of Ser. No. 521,787, filed Aug. 9, 1983, now U.S. Pat. No. 4,489,000 patented Dec. 18, 1984, a process is provided for preparing ceric alkoxides which comprises reacting ceric ammonium nitrate with an alcohol under anhydrous conditions in the presence of an anhydrous base at a temperature within the range from about $-30°$ C. to about 200° C., preferably from about 0° C. to about 150° C., until ceric alkoxide and the nitrate salt of the base are formed.

This process avoids the necessity described by Bradley et al of first preparing the ceric hydroxide from the ceric salt, in their case, ceric ammonium sulphate, and converting the hydroxide subsequently to the chloride, which needs to be stabilized as the pyridine complex. The process of the invention is direct and economical, and in addition utilizes ceric ammonium nitrate, a commercially available material that is relatively inexpensive.

In accordance with the present invention, a process is provided for preparing ceric alkoxides, which comprises reacting ceric ammonium nitrate complexed with and in solution in a glycol ether such as 1,2-dimethoxyethane (DME), 1,2-dimethoxypropane, 1,3-dimethoxypropane (DMP) or tetrahydrofuran, usually in solution in DME or THF, with an anhydrous alkali metal alkoxide at a temperature within the range from about $-30°$ C. to about 200° C., preferably from 0° to about 150° C., until ceric alkoxide and the nitrate salt of the base are formed; the nitrate forming during the reaction is insoluble in the glycol ether and tetrahydrofuran, and can be separated from the reaction mixture, and the cerium alkoxide when soluble in the glycol ether or tetrahydrofuran can be isolated from the solution pure, or as the complex with the alcohol or with the solvent, or in some cases the alkoxides can be used without separation from the reaction mixture in the presence of the nitrates.

DME, DMP and tetrahydrofuran are also excellent solvents for cerium isopropoxide and cerium alkoxides of four or more carbon atoms. This facilitates separation of the cerium alkoxide in working up the reaction mixture, since the inorganic nitrate salt is insoluble in these solvents. Since these solvents are water-soluble, this also suits the resulting cerium alkoxide solutions for sol-gel hydrolytic cleavage process, yielding materials useful in the manufacture of specialty ceramics.

Cerium alkoxides are thought to exist in the form of the alkoxide and as association complexes with free alcohol, or other species used as solvent, as for instance DME, DMP or THF. Mixtures of all of these are what are commonly referred to as "cerium alkoxide", and so the term is used herein in this commonly accepted sense.

The process proceeds will ease with the alkali metal alkoxides of most alcohols, as they can be prepared in these solvents with relative ease. This includes the alkali metal alkoxides of the lower aliphatic alcohols having from one to five carbon atoms, for example, methanol, ethanol, propanol, isopropanol, butanol, isobutanol, sec-butanol, tert-butanol, pentanol, isopentanol, sec-pentanol, and tert-pentanol, as well as the higher aliphatic alcohols having at least six up to about twenty carbon atoms, if desired, such as for example hexanol, heptanol, isoheptanol, octanol, isooctanol, 2-ethyl-hexanol, sec-octanol, tert-octanol, nonanol, isononanol, decanol, dodecanol, tetradecanol, octadecanol, hexadecanol, oleyl alcohol, and eicosyl alcohol; or cycloaliphatic alcohols having from three to about twenty carbon atoms, such as for example cyclopropanol, cyclobutanol, cyclopentanol, cyclohexanol, cycloheptanol, cyclooctanol, cyclododecanol, tripropyl cyclohexanol, methylcyclohexanol and methyl cycloheptanol; or an alkyl aromatic alcohol having from seven to about twenty carbon atoms, such as for example benzyl alcohol, phenethyl alcohol, phenpropyl alcohol, phenoctadecyl alcohol and naphthdecyl alcohol.

The desired alkali metal alkoxide may be purchased or made by any of the known methods. It can be prepared prior to the reaction using NaH, either with an excess of the alcohol, or using the stoichiometric amount of alcohol, in solution in DME, DMP or THF. An excess of the corresponding free alcohol is not necessary, but is not objectionable, and the above-described reactions accordingly can be carried out in the presence of an excess of the alcohol, which is soluble in DME, DMP and tetrahydrofuran, and also in most cases, is a solvent for the corresponding cerium alkoxide.

The solvent can easily be removed from the reaction product after separation of the inorganic alkali metal nitrate, which is a byproduct of the reaction, by distillation at atmospheric or reduced pressure, following completion of the reaction.

The reaction proceeds under anhydrous conditions at a temperature within the range from about $-30°$ C. to about 200° C., preferably from about 0° C. to about 150° C., most preferably at room temperature, depending on the solvent system and alkali metal alkoxide used.

The reaction time is not critical. In the case of the lower alkoxides the reaction is almost instantaneous. The reaction is continued until the desired alkoxide product is formed. This may take from ten minutes to several hours, but it is not necessary to carry the reaction beyond a five hour reaction time. Usually, reaction is complete within from one to three hours.

The reaction can proceed quite rapidly at room temperature, and if it does, it very likely will also proceed at temperatures well below room temperature, down to $-30°$ C., but there is no reason to incur the additional expense of cooling the reaction mixture. The upper limit on reaction temperature is imposed by the volatility of the reaction mixture or any component thereof, and its decomposition temperature. There is no reason to use a temperature above the boiling point of the reaction mixture at atmospheric pressure, but if the boiling temperature is too low, a closed reaction vessel or pressurized system can be used. The reaction temperature need not exceed 200° C., taking the above factors into consideration.

The amount of anhydrous alkali metal alkoxide base is stoichiometric, since the function of the base alkali metal cation is to take up nitrate from the ceric ammonium nitrate starting material:

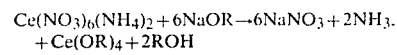
$$Ce(NO_3)_6(NH_4)_2 + 6NaOR \rightarrow 6NaNO_3 + 2NH_3 + Ce(OR)_4 + 2ROH$$

An excess can be used but is not necessary, and in some cases is undesirable, as it might not be easy to separate from the ceric alkoxide.

It can be seen from the equation that there is no need for any additional alcohol. An excess of free alcohol however can be used.

The reaction mixture contains the alkali metal nitrate salt, and this can be separated from the cerium alkoxide during work-up. If this salt is less soluble in the reaction mixture than the alkoxide reaction product, it can be filtered off, and thereby separated from the reaction product. Alternatively, the reaction mixture can be taken up in an inert solvent such as benzene, toluene or hexane, preferably an inert solvent in which the alkoxide reaction product is soluble, and the nitrate salt insoluble, whereupon the nitrate salt is filtered off or centrifuged out.

In the cases of lower alcohols below the isopropoxide, the cerium alkoxide product as well as the alkali metal nitrate are solids and both are insoluble in DME, DMP and tetrahydrofuran. In this case, filtration cannot of course separate the two; the alkoxide reaction product can be recovered and separated from the nitrate salt by extraction with a solvent for the alkoxide in which the nitrate salt is insoluble, using, for example, a Soxhlet apparatus. Alternatively, a solvent for the alkali metal nitrate can be used in which the ceric alkoxide is insoluble. For example, sodium nitrate is soluble in methanol, while ceric tetramethoxide is not, and so in this case sodium nitrate can be separated by extraction with methanol.

Depending on reaction and work-up conditions, the alkoxide can be isolated as associations with one or more molecules of alcohol that generally render it more stable to hydrolytic decomposition. On the other hand, the alkoxide can be isolated in a partially hydrolyzed form, suitable or desirable for certain applications.

For some applications the cerium alkoxides can be used in the form they exist in the reaction mixture at the end of the reaction, without actually isolating them from the reaction mixture, or separating them from the nitrates, which saves processing and handling costs.

The following Examples in the opinion of the inventors represent preferred embodiments of the invention:

EXAMPLE 1

Preparation of Ceric Tetraisopropoxide from Ceric Ammonium Nitrate and Sodium Isopropoxide in 1,2-Dimethoxyethane and IPA a. Reagents:

| Reagents | Wt. (g) | Assay (%) | MWt | Moles | Mole Ratio | Notes |
|---|---|---|---|---|---|---|
| Sodium | 4.14 | — | 22.99 | 0.18 | 6.00 | |
| Isopropyl Alcohol | 55.71 | — | 60.09 | 0.93 | 30.90 | Karl Fisher: 0.123% water |
| Ceric ammonium nitrate | 16.45 | REO = 31.15 | 548.26 | 0.03 | 1.00 | Oven dried, 115° C. |
| 1,2-dimethoxy ethane | 66.15 | — | 90.12 | 0.73 | 24.47 | Dried & distilled over LiAlH$_4$ |

(Sodium and isopropyl alcohol gave 24.73% solution of sodium isopropoxide in isopropyl alcohol).

b. Procedure:

All equipment is oven dried at 115° C. All reactions are run under argon. A 250 ml round bottom flask, charged with isopropyl alcohol inside a glove bag, is brought outside and is equipped with a magnetic stir-bar and Claisen adapter which, in turn, holds a thermometer and a condenser. The condenser is fitted with a T-shaped tube connected to a bubbler and an argon supply. Before opening the reaction flask to add the required amount of sodium, the argon flow is increased. The mixture is refluxed for about 3 hours in order to complete the reaction. The round bottom flask is then taken back into the glove bag (always kept under argon atmosphere). Next, it is equipped with a dropping funnel charged with the orange solution of ceric ammonium nitrate in 1,2-dimethoxyethane. The temperature is kept at above 75° C. The ceric ammonium nitrate solution is slowly added, drop by drop. A mild exothermic reaction occurs as the solution gradually turns yellow and more fluid. A precipitate can be seen in the flask. After the addition is completed the mixture is stirred for one hour and then filtered through a fritted funnel and washed with dimethoxyethane 4 times. The white solid NaNO$_3$ is then dried while the isopropyl alcohol and dimethoxyethane are distilled off from the filtrate. A bright yellow solid, ceric tetraisopropoxide, was thus obtained.

c. Results:

15.2 g of NaNO$_3$ (Theory: 15.3 g) are obtained as a white solid that contains a very small amount of cerium. For the sodium nitrate, the yield is 99.3%. Cerium tetraisopropoxide was isolated as a yellow solid (Found 10.3 g, Theory: 11.29 g). Some was lost during work-up. Ash value of product found: 49.6% theory 45.7%.

EXAMPLE 2

Preparation of Ceric TetraIsopropoxide from Cerium Ammonium Nitrate, Sodium Isopropoxide in 1,2-Dimethoxyethane without free isopropyl alcohol a. Reagents:

| Reagents | Wt. (g) | Assay (%) | MWt | Moles | Ratio | Notes |
|---|---|---|---|---|---|---|
| Sodium | 4.83 | — | 22.99 | 0.21 | 6.00 | |
| Isopropyl Alcohol | 12.62 | — | 60.09 | 0.21 | 6.00 | Karl Fisher: 0.123% water |
| 1,2-Dimethoxy ethane | 50.6 | — | 90.12 | 0.56 | 16.04 | for sodium isopropoxide |
| 1,2-Dimethoxy ethane | 29.4 | — | 90.12 | 0.326 | 9.32 | for ceric ammonium nitrate |
| Ceric ammonium nitrate | 19.2 | REO (31.15) | 548.26 | 0.035 | 1.00 | solution Oven dried, 115° C. | b. Procedure:

A 250 ml round bottom flask, was charged with 12.62 g isopropyl alcohol and 50.6 g 1,2-dimethoxyethane inside a glove bag, was brought outside and equipped with a magnetic stir-bar and Claisen adapter which, in turn, held a thermometer and a condenser. The condenser was fitted with a T-shaped tube connected to a bubbler and an argon supply. Before opening the reaction flask to add the required amount of sodium, the argon flow was increased. The mixture was refluxed at 90° C. for about 24 hours in order to complete the reaction. The round bottom flask was then taken back into the glove bag (always kept under argon atmosphere), and equipped with a dropping funnel charged with the solution of the ceric ammonium nitrate in 29.4 g 1,2-dimethoxyethane. The temperature was maintained above 75° C. while the ceric ammonium nitrate solution was added dropwise. A mild exothermic reaction occurred as the solution gradually turned yellow and more fluid. A precipitate could be seen in the flask. After the addition was completed the mixture is stirred for one hour and the filtered through a fritted funnel and washed with 1,2-dimethoxyethane four times. The while solid NaNO$_3$ was dried while the 1,2-dimethoxyethane was distilled from the filtrate. A bright yellow solid of ceric tetraisopropoxide was obtained.

Results were similar to those obtained in Example 1.

EXAMPLE 3

Preparation of Ceric Tetraisopropoxide from Ceric Ammonium Nitrate and Sodium Isopropoxide in Tetrahydrofuran and IPA a. Reagents:

| Reagents | Wt. (g) | Assay (%) | MWt | Mole | Mole Ratio | Notes |
|---|---|---|---|---|---|---|
| Sodium | 4.14 | — | 22.99 | 0.18 | 6.00 | |
| Isopropyl Alcohol | 59.81 | — | 60.09 | 0.99 | 33.2 | Karl Fisher: 0.123% water |
| Ceric ammonium nitrate | 16.45 | REO = 31.15 | 548.26 | 0.03 | 1.00 | Oven dried, 115° C. |
| Tetrahydrofuran | 72.25 | — | 72.11 | 1.00 | 33.4 | Dried & distilled over LiAlH$_4$ | b. Procedure:

A 250 ml round bottom flask was charged with isopropyl alcohol inside a glove bag, brought outside, and then equipped with a magnetic stir-bar and Claisen adapter, which in turn held a thermometer and a condenser. The condenser was fitted with a T-shaped tube connected to a bubbler and an argon supply. Before opening the reaction flask to add the required amount of sodium, the argon flow was increased. The mixture was refluxed for about 3 hours in order to complete the reaction. The round bottom flask was then taken back into the glove bag (always kept under argon atmosphere). The orange solution of the ceric ammonium nitrate in tetrahydrofuran was added slowly added dropwise through a dropping funnel. The temperature was kept above 75° C. A mild exothermic reaction occurred, as the solution gradually turned yellow and more fluid. A precipitate was observed in the flask. After the addition was completed the mixture was stirred for one hour and then filtered through a fritted funnel and washed with tetrahydrofuran four times. The white solid $NaNO_3$ was dried while the isopropyl alcohol and tetrahydrofuran were distilled off from the filtrate. A bright yellow solid, ceric tetraisopropoxide, was isolated.

Results were similar to those of Example 1.

EXAMPLE 4

Preparation of Ceric Methoxide from Ceric Ammonium Nitrate and Sodium Methoxide in 1,2-Dimethoxyethane a. Reagents:

| Reagents | Wt. (g) | Assay (%) | MWt | Moles | Mole Ratio | Notes |
| --- | --- | --- | --- | --- | --- | --- |
| Sodium Methoxide Solution | 37.98 | 25.6% w/w | 54.02 | .180 | 6.00 | MeOH solution. Commercial grade |
| CAN | 16.45 | REO = 31.15% | 548.26 | .030 | 1.00 | Dried 115° C. |
| DME | 110.9 | — | 90.12 | 1.23 | 41.0 | Dried and distilled over $LiAlH_4$ | b. Procedure:

In an argon-filled glove bag, the ceric ammonium nitrate and 1,2-dimethoxyethane were added to a 250 ml round bottomed flask containing a stir bar. After the ceric ammonium nitrate was dissolved, sodium methoxide solution was added dropwise from an addition funnel with pressure-relief side arm over 15 minutes. The bright yellow slurry was stirred 1 hour. The solids were filtered off, charged immediately to a previously dried Soxhlet apparatus, and extracted with MeOH overnight. The extract was evaporated to dryness to give sodium nitrate, 15.2 g (theory 15.3 g). The thimble, after drying, contained the bright yellow product, cerium tetramethoxide, 7.9 g (theory 7.93 g).

EXAMPLE 5

Preparation of Ceric Butoxide from Ceric Ammonium Nitrate and Sodium Butoxide in 1,2-Dimethoxyethane and n-Butyl Alcohol a. Reagents:

| Reagents | Wt. (g) | Assay (%) | MWt | Moles | Mole Ratio | Notes |
| --- | --- | --- | --- | --- | --- | --- |
| Sodium | 4.14 | — | 22.99 | 0.18 | 6.00 | Solid |
| n-Butyl Alcohol | 52.36 | — | 74.12 | 0.71 | 23.7 | Dried with sodium and distilled |
| CAN | 16.45 | REO = 31.15 | 548.26 | 0.03 | 1.00 | Oven dried, 115° C. |
| DME | 51.45 | — | 90.12 | 0.57 | 19.0 | Dried & distilled over $LiAlH_4$ | b. Procedure:

A 250 ml round bottom flask was charged with n-butanol inside a glove bag, brought outside and was equipped with a magnetic stir-bar and Claisen adapter which, in turn, held a thermometer and a condenser. The condenser was fitted with a T-shaped tube connected to a bubbler and an argon supply. Before opening the reaction flask to add the required amount of sodium, the argon flow was increased. The mixture was refluxed at 118° C. to complete the reaction. The round bottom flask was then taken back into the glove bag (always kept under argon atmosphere). The orange solution of the ceric ammonium nitrate in 1,2-dimethoxyethane was added through a dropping funnel. The temperature was kept above 75° C. while the ceric ammonium nitrate solution was slowly added, dropwise. A mild exothermic reaction occurred as the solution gradually turned yellow and more fluid. A precipitate could be seen in the flask. After the addition was completed the mixture was stirred for one hour. The $NaNO_3$ was filtered off and washed with 1,2-dimethoxyethane four times. Found 15.3 g, theory 15.3. The yellow filtrate was concentrated under reduced pressure to give ceric tetrabutoxide as a bright yellow solid, 12.8 g (theory 12.9 g).

Having regard to the foregoing disclosure the following is claimed as inventive and patentable embodiments thereof:

1. A process for preparing ceric alkoxides which comprises reacting ceric ammonium nitrate complexed with and in solution in a solvent selected from the group consisting of 1,2-dimethoxyethane, 1,2-dimethoxypropane, 1,3-dimethoxypropane and tetrahydrofuran with an alkali metal alkoxide under anhydrous conditions at a temperature within the range from about −30° to about 200° C. until ceric alkoxide and the nitrate salt of the alkali metal are formed.

2. A process according to claim 1 in which the alcohol corresponding to the alkali metal alkoxide is present in the reaction mixture.

3. A process according to claim 1 in which the alkali metal alkoxide is of an alcohol having from one and up to about twenty carbon atoms.

4. A process according to claim 1 in which the alcohol is a cycloaliphatic alcohol having from four to about twenty carbon atoms.

5. A process according to claim 1 in which the alcohol is an alkyl aromatic alcohol having from seven to about twenty carbon atoms.

6. A process according to claim 1 in which the alcohol is selected from the group consisting of higher aliphatic alcohols having at least six up to about twenty carbon atoms; cycloaliphatic atoms having from three to about twenty carbon atoms; alkyl aromatic alcohols having from seven to about twenty carbon atoms; and is incorporated directly in the reaction mixture together with a lower aliphatic alcohol having from one to five carbon atoms.

7. A process according to claim 1 in which the solvent is 1,2-dimethoxyethane.

8. A process according to claim 1 in which the solvent is 1,3-dimethoxypropane.

9. A process according to claim 1 in which the solvent is tetrahydrofuran.

10. A process according to claim 1 in which the solvent is 1,2-dimethoxypropane.

* * * * *